US009066897B2

(12) United States Patent
Mendoza et al.

(10) Patent No.: US 9,066,897 B2
(45) Date of Patent: Jun. 30, 2015

(54) PYTHIUM IMMUNOTHERAPY

(75) Inventors: Alberto L. Mendoza, Haslett, MI (US); Robert L. Glass, Hutto, TX (US); Richard D. Hansen, Mustang, OK (US)

(73) Assignee: Board of Trustees of Michigan State University, Lansing, MI (US)

( * ) Notice: Subject to any disclaimer, the term of this patent is extended or adjusted under 35 U.S.C. 154(b) by 0 days.

(21) Appl. No.: 12/647,971

(22) Filed: Dec. 28, 2009

(65) Prior Publication Data

US 2011/0159042 A1 Jun. 30, 2011

(51) Int. Cl.

| | |
|---|---|
| ***A61K 39/00*** | (2006.01) |
| ***A01N 65/00*** | (2009.01) |
| ***A61K 36/06*** | (2006.01) |
| ***A61K 36/09*** | (2006.01) |
| ***A61K 39/35*** | (2006.01) |
| ***A61K 39/39*** | (2006.01) |
| *A61K 36/07* | (2006.01) |

(52) U.S. Cl.

CPC ............. *A61K 39/0002* (2013.01); *A61K 36/07* (2013.01); *A61K 39/35* (2013.01); *A61K 39/39* (2013.01); *A61K 2039/545* (2013.01); *C12N 2710/20011* (2013.01)

(58) Field of Classification Search

CPC .. A61K 39/0002; A61K 36/07; A61K 36/074
See application file for complete search history.

(56) References Cited

U.S. PATENT DOCUMENTS

| | | | |
|---|---|---|---|
| 5,948,413 | A | 9/1999 | Mendoza |
| 6,287,573 | B1 | 9/2001 | Mendoza |
| 6,833,136 | B2 | 12/2004 | Mendoza |

OTHER PUBLICATIONS

Chindamporn et al. (Clinical and Vaccine Immunology, Mar. 2009; 16(3): 330-336).*

Gaastra et al., Veterinary Microbiology, Nov. 2010; 146: 1-16.*

Bertone (The Veterinary Clinics of North America: Equine Practice, 1989; 5(3): 551-562).*

Judy (Anhidrosis in Horses, Jul. 2010, suite101.com; pp. 1-2).*

Moore (Cutaneous Mast Cell Tumors in Dogs, 2005, 30th World Congress of the World Small Animal Veterinary Association; pp. 1-5).*

Camus et al. (J. Vet. Diagn. Invest, 2004; 16: 567-571).*

Laohapensang et al. (International Journal of Angiology, 2005; 14: 123-128).*

Ameen, Tropical Doctor, Apr. 2010; 40: 65-67.*

Chambers et al., Journal of General Virology, 2003; 84: 1055-1062.*

Heath Line, (no publication date) Kentucky Equine Research Review; 2 pages.*

Krajaejun et al., Journal of Clinical Microbiology, 2006; 44(5): 1674-1680.*

Leal et al., Journal de Mycologie Medicale, 2005; 15: 63-68.*

Chindamporn, Ariya et al., "Antibodies in the Sear of Host Species with Pythiosis Recognize a Variety of Unique Immunogens in Geographically Divergent *Pythium insidiosum* Strains", Clinical and Vaccine Immunology, 16 (3):330-336 (2009).

* cited by examiner

*Primary Examiner* — Gary Nickol
*Assistant Examiner* — Lakia Tongue
(74) *Attorney, Agent, or Firm* — McKee, Voorhees & Sease, PLC

(57) ABSTRACT

A method and vaccine for modulating the immune system of animals with diseases other than caused by *P. insidiosum*, comprising administering to the animal immune modulating effective amount of the *P. insidiosum*, Strain MTPI-04. The vaccine uses an immune response that effectively treats and manages a variety of human and animal diseases.

6 Claims, No Drawings

PYTHIUM IMMUNOTHERAPY

BACKGROUND OF THE INVENTION

This invention relates to the continued exploration of *Pythium insidiosum*, its use as an antigen for prophylactic and therapeutic vaccines and to isolation methods for it. In prior inventions of Dr. Alberto L. Mendoza and other co-inventors with him *P. insidiosum* protein was used for treatment of *P. insidiosum* infection in humans and other animals, see for example, U.S. Pat. No. 5,948,413 of Sep. 7, 1999; U.S. Pat. No. 6,287,573 of Sep. 11, 2001; and U.S. Pat. No. 6,833,136 of Dec. 21, 2004. In each instance, the fungal-like strain there used was eventually used either alone or with other cells to treat Pythiosis, both in humans and other animals. The particular fungal-like strains there used were deposited in the American Type Culture Collection under the Budapest Treaty as ATCC 74446 and/or ATCC 58643. The animals treated in those patents included humans, horses, dogs and cats. In every instance in each one of these patents an objective was to prepare a vaccine from *Pythium insidiosum* to provide a beneficial immunological response for treating or preventing Pythiosis. The disclosure of U.S. Pat. Nos. 5,948,413; 6,287,573; and 6,833,136 are incorporated herein by reference.

Dr. Mendoza and his colleagues have continued working with *P. insidiosum* in an effort to improve upon the inventions of their earlier patents. Improvement can come in a variety of ways when dealing with vaccines. One way of improvement is in the effectiveness of specific disease treatment or prevention. Another way to improve is to widen the scope of diseases that can be effectively treated or prevented with a vaccine. A still further way to improve a vaccine is to widen the number of species that can be treated with it. The present invention has as its primary objective both widening the number of species that can be treated with *P. insidiosum* protein and widening the scope of diseases that can be effectively treated by modulating the immune response in an animal.

It goes without saying that there is a continuing need for vaccines that are effective and provide an efficient modulated immune response to effectively treat a variety of diseases in a variety of different species.

BRIEF SUMMARY OF THE INVENTION

The present invention provides a *pythium* immunotherapy produced from *Pythium insidiosum* Strain MTPI-04 (Texas strain) by isolation and concentration of soluble proteins. This strain-specific *pythium* immunotherapy is comprised of all proteins found in *Pythium* allergenic extract (PAE) described in Dr. Mendoza's earlier patents, but additionally contains various other proteins, including a significantly greater quantity of 28 kDa protein expressed by MTPI-04. In short the expressed protein profile is quite different in this case.

DETAILED DESCRIPTION OF THE PREFERRED EMBODIMENTS

This invention relates to a *pythium* immunotherapy product which may be administered by injection, for example.

As used herein, *Pythium insidiosum* Strain MTPI-04 (Texas strain) refers to Strain MTPI-04 or any variant or derivative or analog strain thereof which produces an equivalent immune modulating effective response; that is a response that can be used to provide a *pythium* immunotherapy demonstrated benefit for treatment of, or managing diseases other than caused by *Pythium insidiosum*, such as for example: Sarcoid (Equine); Mast cell tumor (Canine); Allergic Disease (Canine, Feline, Equine, Human); Inflammatory Bowel Disease (Canine); Miliary dermatitis (Feline); Exuberant Granulation (Equine); Chromoblastomycosis (Human); Asthma (Feline); Otitis Externa (Canine, Feline); Arthritis (Canine); Anhidrosis (Equine); and Navicular Disease and Laminitis (Equine).

It is not known what is peculiar and unique about the *P. insidiosum* Strain MTPI-04 (Texas strain) that allows it to effectively modulate immune systems, and provide immunotherapy for diseases beyond those caused by *Pythium insidiosum*. While Applicant does not wish to be bound by any theory, it is possible that the other proteins expressed than those expressed by the strains used in our earlier patents, and/or that the different ratios of protein may be factors. For example, it has been observed that there is a significantly greater quantity of 28 kDa protein, and that the expression of a protein at approximately 124 kDa appears to be unique to Strain MTPI-04 (Texas strain). See Chindamporn et al., Clinical Vaccine Immunology, *Antibodies in the Sera of Host Species with Pythiosis Recognize a Variety of Unique Immunogens in Geographically Divergent Pythium insidiosum Strains*, Vol. 16, No. 3, pp. 330-36, Table 3 MTPI-04 at page 334.

With regard to *P. insidiosum*, Strain MTPI-04, Applicants assert that upon allowance of claims, Applicants will deposit *P. insidiosum*, Strain MTPI-04, as described in this originally filed specification, and will amend claims as necessary insert the ATCC number into the claims. Applicants further provide assurance that:

a) during the pendency of this application access to the invention will be afforded to the Commissioner upon request;
b) all restrictions upon availability to the public will be irrevocably removed upon granting of the patent;
c) the deposit will be maintained in a public depository for a period of thirty years, or five years after the last request for the enforceable life of the patent, whichever is longer;
d) a test of the viability of the biological material at the time of deposit will be conducted (see 37 C.F.R. §1/807); and
e) the deposit will be replaced if it should ever become non-viable.

Applicants submit this offer of deposit completes requirements of 35 U.S.C. §112 with respect to *Pythium insidiosum*, Strain MTPI-04, and all requirements of 37 C.F.R. §§1.801-1.809 are met.

While the hereinafter description is given primarily in conjunction with injectable vaccines in sterile aqueous solution, the vaccine can be administered in other ways such as needleless injection, a solid dose implant, topically or even by oral, ocular, inhalation or suppository administration.

The process of producing the vaccine begins by growing cells of *Pythium insidiosum* Strain MTPI-04 in a culture medium. The preparation of the stock culture, seed inoculums and finished product can occur in the following manner. For convenience the steps are categorized and numbered.

Growth of Cultures

1. Cultures of Strain MTPI-04 are stored/maintained in either of the following three (3) forms:
   a. Lyophilized
   b. Frozen
   c. Hyphae culture maintained on Corn Meal Agar (CMA) or Sabouraud Dextrose Agar (SDA)
2. An SDA plate is inoculated with one of the above and incubated at 37° C. for approximately 24 hours. This represents Production Culture #1.

3. Transfer a portion of the hyphae colony to another SDA plate and incubate another 24 hours at 37° C. This represents Production Culture #2.
4. Transfer a portion of the hyphae colony to another SDA plate and incubate another 24 hours at 37° C. This represents Production Culture #3. By this third culture, the hypae should be healthy and ready to be inoculated into liquid media.
5. Prepare shaker flask(s) of sterile Sabouraud Dextrose Broth (SDB), filling them to half of their full volume.
6. Inoculate the flask(s) containing warm (37° C.) SDB with a portion of Production Culture #3. Incubate the flask(s) at 37° C. on a rotating shaker device at approximately 150 rpm for 5 to 7 days until the culture has a confluent hyphae mat.

Protein Extraction

1. Aseptically transfer culture fluids to the filter housing of a sterile vacuum/bottle top filter apparatus equipped with a clarifying filter. Upon applying a vacuum to the receiver bottle cap arm, hyphae remain above the filter and the fluid containing soluble extracellular proteins (filtrate) collects in the receiver bottle below. Record the filtrate volume and store at 2 to 7° C.
2. Hyphae are aseptically transferred to a sterile pre-chilled mortar containing liquid nitrogen. This rapid freezing effectively inactivates the *Pythium insidiosum* culture. A sterile pestle is used to disrupt the cells and turn the mass into a powder. The powder is suspended in sterile deionized water, mixed well and incubated at 2 to 7° C. for 1 hour. The ground hyphae-in-water suspension contains both soluble intracellular proteins and insoluble hyphae fragments.
3. The suspension is centrifuged at approximately 750×g for 1 hour, then the supernatant containing soluble intracellular proteins collected and stored at 2 to 7° C.
4. The filtrate from Step 1 above and the supernatant from Step 3 above are combined and poured into an Erlenmeyer flask and acetone added until the suspension becomes milky-white in appearance. This suspension is placed at 2° to 7° C. until clearing occurs and the extracellular protein collects at the bottom of the flask.
5. Carefully decant the acetone supernatant and allow the precipitate to air dry at room temperature under a fume hood for 20 minutes to vaporize all remaining acetone.
6. Collect the precipitated protein with a volume of sterile deionized water sufficient to dissolve the precipitate and hold at 2 to 7° C. for 24 hours to dissolve soluble proteins.
7. Centrifuge the mixture of soluble intracellular and extracellular proteins at 750×g for 30 minutes. Collect the supernatant containing only the soluble proteins and discard the precipitate containing any remaining insoluble proteins.
8. Diafilter the supernatant under refrigeration using a sterile filter housing equipped with a 10,000 MWCO non-protein binding filter. The filtrate is discarded and the retentate stored refrigerated at 2 to 7° C. or held frozen until finished product is to be prepared.
9. Before storing the concentrate, sample, measure and record the total combined extracellular/intracellular protein.

Preparation of Finished Product

1. Dilute the concentrate with sterile saline to the desired protein level, then measure once more to confirm.
2. Fill multiple or single unit dose sterile vials with finished product. A 0.2 micron filter is incorporated in-line to help assure product sterility.
3. Apply sterile stoppers to the vials, then secure with aluminum seals.

A primary difference exists in the method of production and isolation of the present invention strain from that used in previous Mendoza et al. patents, namely, the method of production in the new product is different than that of the previous patents in the following ways:

1. The MTPI-04 strain is used rather than the MTPI-19 strain (ATCC 74446 and/or ATCC 58643); and
2. Cryogenic destruction of the hyphae is used to inactivate the *Pythium* culture, rather than using a chemical agent.

Preferably the immunotherapeutic concentrate contains between about 20 mcg to 5.0 mg of protein per dose. The immunotherapeutic dosage preferred for some animals is between about 20 mcg/mL and 40 mcg/mL.

The immunotherapeutic of the present invention is preferably injected intramuscularly. The vaccine can also be administered intradermally or subcutaneously by needle or needleless methods.

A sterile carrier is used in the immunotherapeutic. The preferred carrier is water or an aqueous saline solution, particularly in humans.

The immunotherapeutic can be combined with immunizing components for other diseases to produce a multivalent vaccine.

In the following examples, the improved immunotherapeutic was prepared from *P. insidiosum* Strain MTPI-04 cultured, isolated, extracted and stored as previously described. It was stored at 2 to 7° C. until use.

For all Examples below the carrier was saline solution and for Examples 3-4, and 6-12 each dose was 40 mcg.

EXAMPLE 1

Human

A. Chromoblastomycosis

A 74-year-old Brazilian man had a 54-year history of a chromoblastomycosis fungal infection of his right arm. The patient had been treated several times over the years with antifungal drugs including Itraconazole, Ketoconazole and Amphotericin B without success. He entered the Institute of Dermatology (ISMD) in Belo Horizonte, Brazil because the lesions on his arm were increasing in size. Based upon the long history of unsuccessful treatments with conventional antifungal drugs, treatment began using injections of the *Pythium* Immunotherapeutic product derived from Strain MTPI-04 at 20 mcg/dose, injected subcutaneously, one week apart for a month. There was dramatic reduction in lesion size during the initial 7-month treatment period. Since the ISMD still found “sclerotic bodies” on some small residual lesions during the patient’s last visit of Dec. 11, 2009, this suggests the infection is still present at a lower level but the treatment appears to have diminished and controlled the disease progression. Immunotherapy has begun again with the patient scheduled to visit the ISMD during February, 2010.

EXAMPLE 2

Equine

A. Sarcoids

The equine sarcoid is the most common skin tumor of horses worldwide. These locally aggressive benign tumors are widely accepted to be associated with bovine papillomavirus. Four (4) veterinarians treating a total of 6 cases of equine sarcoid disease with subcutaneous injections of the

*Pythium* Immunotherapeutic (20 mcg/dose) reported complete resolution of sarcoid lesions in 4 cases and 50% reduction of lesions in the remaining 2 cases.

EXAMPLE 3

B. Exuberant Granulation ("Proud Flesh")

A 30-year-old mare experienced a wound on her right rear leg over the proximal metatarsal bone that subsequently healed with excessive granulation, confirmed by histopathology. Following sharp resection of the 10 cm tumor, a series of 4 weekly intramuscular injections of the *Pythium* Immunotherapeutic were given. Without ancillary treatment, the lesion healed completely over a period of 5 months. The horse subsequently grew an extremely thick winter coat, something she had not done for many years.

EXAMPLE 4

C. Laminitis

A horse with a history of minor lameness due to navicular disease was also diagnosed with laminitis. The patient was given 3 weekly injections of the *Pythium* Immunotherapeutic. Lameness resolution was noted within 24 hours following each treatment, however lameness returned by day 6 following each treatment. An additional course of 3 weekly injections were given, this time the horse was not ridden during the treatment period. Approximately 90% clinical recovery was noted and the patient continued to improve.

EXAMPLE 5

D. Allergy

A horse with a history of atopic signs and concurrent high serum IgE antibody levels against multiple allergens was treated with a combination of *Pythium* Immunotherapeutic subcutaneously at 20 mcg/dose and various allergenic extract injections on days 1, 14 and 30. Serum IgE specific for the allergens used in the treatment set showed substantially reduced levels on day 30. By day 60, serum IgE was within normal limits and atopic clinical signs were resolved.

EXAMPLE 6

E. Anhidrosis

A horse with a 2-year history of clinical anhidrosis (not able to perspire) was given 3 subcutaneous injections (days 1, 7 and 21) of the *Pythium* Immunotherapeutic, 40 mcg/dose. Seven (7) days after the $3^{rd}$ treatment, the horse perspired normally during exercise. The attending veterinarian reports the patient continues to perspire normally during exercise at 90 days following the $3^{rd}$ injection.

EXAMPLE 7

Canine

A. Mast Cell Tumor

A 12-year-old spayed female mix breed dog had six (6) mast cell tumors (MCT's) surgically excised over a 2 year period. A new MCT measuring 4-5 cm in diameter and soft appeared on her dorsal withers and the owner refused further surgery. Subcutaneous *Pythium* Immunotherapy was started and one week later when presented for a $2^{nd}$ treatment, the tumor measured 2×3 cm and was hard. At $3^{rd}$ treatment, one week later, the tumor was circular, measuring 1.5 cm in diameter and 0.5 cm thick and was very hard. At $4^{th}$ treatment one week later, the tumor was 1.25 cm diameter and 0.5 cm thick and was very hard and non-painful. Administration was by subcutaneous injection. One week after the $4^{th}$ treatment, the tumor continued to shrink to 1.0 cm diameter and later disappeared. No further MCT's have recurred.

EXAMPLE 8

B. Allergy & Otitis Externa

An 8-year-old intact female Cocker Spaniel suffered with severe skin allergies most of her life. Her ears were especially nasty and were filled with purulent discharge and she had a large skin lesion on her chest that refused to heal. The dog was given weekly subcutaneous injections of the *Pythium* Immunotherapeutic for 4 weeks, but improvement was marked at 1 week following the initial treatment: The chest lesion was healed and the ears were clinically normal, i.e. no inflammation, no discharge and no odor. Upon $4^{th}$ injection the ears still appeared normal.

EXAMPLE 9

C. Arthritis

A 5-year-old neutered male Sheltie had congenital hip dysplasia and extreme recurrent skin allergies. He was treated with four subcutaneous weekly injections. Five (5) days following the first subcutaneous injection with the *Pythium* Immunotherapeutic, the dog was not itching at all and acting as if his hips were not bothering him. At the time of the last injection, the dog continued to be very active although he still was a little slow in getting up after resting. There were no apparent allergic skin problems. A year later the owner reported he was much better, with only mild allergic problems requiring antihistamines and his arthritis remains much improved.

EXAMPLE 10

D. Inflammatory Bowel Disease

A 10-year-old neutered male terrier mix with Inflammatory Bowel Disease (IBD) had continuing bouts of vomiting and diarrhea. He was treated with four subcutaneous weekly injections. The clinical signs improved markedly following the initial subcutaneous injection with the *Pythium* Immunotherapeutic and the dog had no more gastrointestinal episodes, was much calmer and gained 1.7 pounds at the time he was presented for a $3^{rd}$ treatment.

EXAMPLE 11

Feline

A. Asthma

A 10-year-old spayed female Siamese cat had respiratory problems consistent with feline asthma for about 2 years. She was treated with four subcutaneous weekly injections. At the time of the initial *Pythium* Immunotherapy injection, the cat had severe expiratory dyspnea. At second injection, the cat still had slight dyspnea but not nearly as severe. The cat was clinically normal, without dyspnea, when presented for her 3rd injection.

EXAMPLE 12

B. Miliary Dermatitis

A 10-year-old neutered male Manx cat exhibited extreme miliary dermatitis lesions. He was alopecic and had very itchy, dry, flaky skin over about 70% of his body. Subcutaneous *Pythium* Immunotherapy was begun. At 2nd treatment the alopecia started to resolve and the skin was not as hot and inflamed. After a total of 8 weekly treatments, the hair had re-grown, the skin was normal and the cat was not scratching at all. There remained a small area of alopecia over the caudal ventral abdomen.

The invention has been shown and described above with the preferred embodiments, and it is understood that many modifications, substitutions, and additions may be made, which are within the intended spirit and scope of the invention. From the foregoing, it can be seen that the present invention accomplishes at least all of its stated objectives.

What is claimed is:

1. A method of reduction of lesions associated with equine sarcoids by *Pythium insidiosum* (*P. insidiosum*), comprising:

injecting into an equine animal not suffering from *P. insidiosum* infection or allergy, to treat equine sarcoids, proteins expressed from *P. insidiosum* MTPI-04, ATCC-PTA-12166 to generate a therapeutic response within the animal.

2. The method claim 1 wherein the proteins are ones expressed from *P. insidiosum*, MTPI-04 in a sterile carrier.

3. The method of claim 2 wherein the sterile carrier is an aqueous saline solution.

4. The method of claim 1 wherein each dose given has from about 20 meg to 5 mg of said expressed proteins.

5. The method of claim 1 wherein the dose level given to said animal is from about 20 mcg/mL to about 40 mcg/mL.

6. A method of reducing the size of lesions in a patient with chromoblastomycosis fungal infection, comprising:

injecting into said patient not suffering from *P. insidiosum* infection of allergy to treat chromoblastomycosis fungal infection proteins expressed from *P. insidiosum* MTPI-04, ATCC-PTA-12166 to generate a therapeutic response within said patient.

* * * * *

UNITED STATES PATENT AND TRADEMARK OFFICE

CERTIFICATE OF CORRECTION

PATENT NO. : 9,066,897 B2
APPLICATION NO. : 12/647971
DATED : June 30, 2015
INVENTOR(S) : Mendoza et al.

It is certified that error appears in the above-identified patent and that said Letters Patent is hereby corrected as shown below:

Col. 8, Claim 4, Line 14:
DELETE after 20 “meg”
INSERT after 20 --mcg--

Signed and Sealed this
First Day of December, 2015

Michelle K. Lee
*Director of the United States Patent and Trademark Office*